United States Patent [19]

Kameswaran

[11] 4,454,344

[45] Jun. 12, 1984

[54] METHOD FOR THE RESOLUTION OF RACEMIC 2-(p-DIFLUOROMETHOXY-PHENYL)-3-METHYLBUTYRIC ACID

[75] Inventor: Venkataraman Kameswaran, Princeton Junction, N.J.

[73] Assignee: American Cyanamid Company, Stamford, Conn.

[21] Appl. No.: 410,805

[22] Filed: Aug. 23, 1982

[51] Int. Cl.$^3$ .............................................. C07B 19/00
[52] U.S. Cl. .................................... 562/401; 562/472
[58] Field of Search ................................ 562/401, 472

[56] References Cited

U.S. PATENT DOCUMENTS 4,178,460  12/1979  Berkelhammer et al. ...... 562/401 X
4,237,313  12/1980  Higo et al. .......................... 562/401

*Primary Examiner*—Natalie Trousof
*Assistant Examiner*—Vera C. Clarke
*Attorney, Agent, or Firm*—Estelle J. Tsevdos; H. G. Jackson

[57] ABSTRACT

A method for the resolution of racemic 2-(p-difluoromethoxyphenyl)-3-methylbutyric acid into its optically active components. The method utilizes salts prepared by reacting the racemic acid with optically active amines and recovers the dextrorotatory isomer. The present invention also relates to insecticidal pyrethroids prepared from (+)-2-(p-difluoromethoxyphenyl)-3-methylbutyric acid.

5 Claims, No Drawings

METHOD FOR THE RESOLUTION OF RACEMIC 2-(P-DIFLUOROMETHOXYPHENYL)-3-METHYL-BUTYRIC ACID

The invention herein described relates to a method for the resolution of racemic 2-(p-difluoromethoxyphenyl)-3-methylbutyric acid and the recovery of the dextrorotatory isomer thereof. The method uses an optically active amine to form an optically active salt of dextrorotary 2-p-difluoromethoxyphenyl)-3-methylbutyric acid and isolates the resultant salt from the reaction mixture. Using a decomposition reaction, the dextrorotary salt is then regenerated from the amine salt.

By way of background, the racemic 2-(p-difluoromethoxyphenyl)-3-methylbutyric acid and especially the dextrorotary (+) isomer thereof are useful and valuable intermediates for the preparation of pyrethroid type pesticides. Pesticidal pyrethroids are disclosed and claimed in U.S. Pat. No. 4,199,595, incorporated herein by way of reference. Pyrethroid pesticides are valuable and highly effective chemicals for the control of various insects and other pests, particularly those which cause significant economic damage to field crops and livestock.

In light of the foregoing discussion of the desirability of obtaining pyrethroid pesticides for control of noxious pests, it is necessary to obtain the chemical intermediates which are involved in the synthesis of these products. Accordingly, an object of this invention is to provide a method for the resolution of racemic 2-(p-difluoromethoxphenyl)-3-methylbutyric acid and recovery of the dextrorotary isomer of this acid. This object is manifest in the following description and particularly delineated in the appended claims.

A method for the resolution of racemic 2-(p-difluoromethoxyphenyl)-3-methylbutyric acid has been unexpectedly discovered. This racemic acid and its optical isomers may be graphically represented by structural formula-(I) wherein the asterisk indicates the location of the chiral center in said structure:

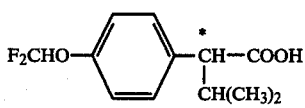

(I)

One of the valuable pyrethroid pesticides cited in U.S. Pat. No. 4,199,595 may be prepared from the acid of formula-(I) by the following route:

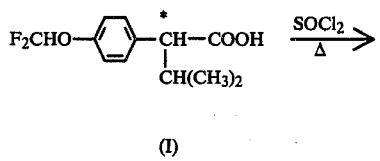

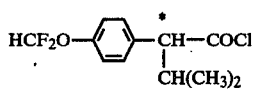

(II)

$$II + HO-\underset{CN}{\underset{|}{CH}}-\text{\Large\textcircled{}}-O-\text{\Large\textcircled{}} \quad (III)$$

↓ acid acceptor $$F_2CHO-\text{\Large\textcircled{}}-\underset{CH(CH_3)_2}{\underset{|}{\overset{*}{CH}}}-CO-O-\underset{CN}{\underset{|}{\overset{*}{CH}}}-\text{\Large\textcircled{}}-O-\text{\Large\textcircled{}}$$

IV

The pyrethroid of formula-(IV) possesses two chiral centers which are indicated by asterisks in the above structure. Therefore, if it is prepared from the unresolved acid of formula-(I) and the unresolved -cyano-m-phenoxybenzyl alcohol of formula-(III), it will be a mixture of four optical isomers. However, since the insecticidal-pesticidal activity of the pyrethroid of formula-(IV) increases twofold when prepared from the resolved dextrorotary (+) acid of formula-(I) (c.f., U.S. Pat. No. 4,199,595), it is desirable to prepare this pyrethroid using (+)-2-(p-difluoromethoxyphenyl)3-methylbutyric acid.

Thus, the formula-(I) racemic acid, i.e., (±)-2-(p-difluoromethoxyphenyl)-3-methylbutyric acid, may be resolved by the method of the invention as follows:

One molar equivalent of the racemic acid of formula-(I) is dissolved in a water immiscible solvent selected from benzene, toluene, xylene, or mixtures thereof. To the above solution is then added about 40 to 100 mol percent, preferably 50 to 70 mol percent, of (−)-α-phenethylamine, and about 30 to 60 mol percent of an aqueous solution of a base selected from alkali metal hydroxides, carbonates, bicarbonates, and ammonium hydroxide. If so desired, additional water may also be incorporated into the above reaction mixture, above and beyond the amounts already present in said aqueous base. Next, this reaction mixture is stirred and heated at a temperature ranging from about 40° C. to the boiling point of said reaction mixture at atmospheric pressure for a period of time sufficient to convert essentially all of the (+) acid present to its (−) -α-phenethylamine salt. The reaction mixture is cooled. The precipitated (−)-α-phenethylamine salt of (+)-2-(p-difluoromethoxyphenyl)-3-methylbutyric acid is then removed from the reaction mixture and purified by standard laboratory procedures (i.e., recrystallization) if so desired.

Finally, the (+)-2-(p-diflouromethoxyphenyl)-3-methylbutyric acid is regenerated from the above salt by stirring with a mixture of a water immiscible solvent selected from the group listed above, a dilute acid (i.e., dilute sulfuric or hydrochloric acid used in excess over theory) and additional water if so desired. The thus regenerated formula-(I) dextrorotatory acid is present in the solvent phase and may be isolated therefrom by standard laboratory procedures, or said solution may be used directly for the preparation of the formula-(IV) pyrethroid.

Advantageously, the method of the present invention employs a two phase solvent system, the use of which affords the desired (+)-acid in improved yields when compared to yields obtainable by conventional procedures used to resolve such racemates.

Other resolving agents which may be utilized to good advantage in the above-described process for the isolation of the (+)-formula-(I) acid may be selected from the group consisting of: (+) and (−)-2-amino-1-butanol, dehydroabietylamine, (+) and (−)-α-4-bromophenylethylamine, (−)-α-(1-naphthyl)ethylamine, 1-Ephedrine, 1S-2S-(+)-2-amino-1-phenyl-1,3-propanediol, (+) and (−)-2-(4-chlorobenzylamino)-1-butanol, (+) and (−)-2-(4-thiobenzylamino)-1-butanol, (+) and (−)-2-(3-nitrobenzylamino)-1-butanol, and (+) and (−)-2-(2,5-dimethylbenzylamino)-1-butanol.

Preferably, the racemic acid of formula-(I) is dissolved in a toluene/water mixture having a weight ratio of about 40/60 to 60/40, and preferably having a weight ratio of 50/50 to 55/45.

To the above two-phase mixture is then added (−)-α-phenethylamine in amounts from about 50 to 70 mol percent (preferably 60 to 70 mol percent), and sodium hydroxide in amounts from about 30 to 50 mol percent, wherein the sum of these two components is preferably 100 mol percent. The reaction mixture is then stirred and heated at a temperature ranging from about 40° C. to 100° C. (preferably from about 70° to 80° C.) for a period of time sufficient to complete the formation of the (−)-α-phenethylamine salt of (+)-2-(p-difluoromethoxyphenyl)-3-methylbutyric acid. The reaction mixture is then cooled and the aqueous phase is separated from the toluene phase which contains the above salt. The salt may be isolated from the organic phase by conventional methods (i.e., filtration) and used without further purification, or it may be purified by standard methods (i.e., recrystallization) if so desired.

Finally, the salt is decomposed with dilute sulfuric acid, or dilute hydrochloric acid, in the presence of toluene and water to yield the desired (+)-2-(p-difluoromethoxyphenyl)-3-methylbutyric acid of formula-(I) dissolved in the toluene phase. The solution is dried and the acid isolated therefrom, or the solution may be used directly in the preparation of the pyrethroid of formula-(IV) as follows:

To the solution of the (+)-formula-(I) acid in toluene is added thionyl chloride in amounts in excess over theory. The mixture is then heated at reflux until essentially all of the carboxylic acid of formula-(I) is converted to the corresponding acid chloride of formula-(II). Next, the excess thionyl chloride is removed from the reaction mixture, and the acid chloride isolated by removal of the solvent under vacuum, or if so desired, the solution of said formula-(II) acid chloride may be used directly. Finally, the acid chloride is reacted with (±)-α-cyano-m-phenoxybenzyl alcohol in the presence of toluene and pyridine to yield the pyrethroid of formula-(IV).

As stated above, the thus obtained pyrethroid is characterized by a pesticidal activity increased twofold over that of the analog prepared from the unresolved formula-(I) acid.

The following Examples further serve to illustrate the invention and are not intended to be limitative thereof.

EXAMPLE 1

Preparation of the (−)-α-phenethylamine salt of (+)-2-(p-difluoromethoxyphenyl)-3-methylbutyric acid A solution of (±)-2-(p-difluoromethoxyphenyl)3-methylbutyric acid in toluene (9.0 kg as is, 3.75 kg crude acid=3.1 kg pure; 12.5 mol), water (6.75 l), and toluene (3.75 l), and 50% sodium hydroxide (608 g=398 ml =7.6 mol) is stirred, heated to 84° to 86° C. and a solution of (−)-α-phenethylamine (PEA: 921 g, 7.6 mol) in toluene (9.57 l) is added over a 10 to 15 minute period. Shortly after the addition is completed, the title product precipitates. The reaction mixture is held for one hour at reflux and is then cooled at 40° to 45° and allowed to settle. Next, the aqueous phase is removed, the toluene layer (a slurry) is washed with 10% sodium chloride, or sodium sulfate solution (5.0 kg), the aqueous wash is removed and toluene (6.25 l) is added to the organic phase. The mixture is heated to reflux and held at reflux for 1.5 hours. It is then cooled to 40° C. and filtered. The filter cake is washed with water (6.5 l) and toluene (6.5 l), and is then used without drying in the next reaction step.

EXAMPLE 2

Preparation of (+)-2-(p-difluoromethoxyphenyl)-3-methylbutyric acid

The wet filter cake obtained by the preparation of Example 1 is added slowly to a well stirred mixture of toluene (1.75 l) and 20% aqueous sulfuric acid (2.7 kg; 2.37 l) at below 45° C. After stirring the mixture for a short period of time, the layers are allowed to settle (the pH of the aqueous layer must be <2). The aqeous layer is then separated and the toluene layer containing the title product may be used without further purification in the reaction yielding the pyrethroid insecticide.

In the above reaction, the title product is obtained in 80% yield as calculated from optical rotation data.

EXAMPLE 3

Evaluation of the effect of various PEA/NaOH ratios on the optical purity and yield of (+)-2-(p-difluoromethoxyphenyl)-3-methylbutyric acid By the method of Examples 1 and 2, a number of preparations are run in toluene/water media using various mol percent ratios of (−)-α-phenethylamine (PEA) and sodium hydroxide. Pertinent data and the results of these preparations are summarized in Table I below.

It can be clearly seen from Table I that the best yields of highly pure (optically) products are obtained when the amount of PEA is from about 50 to 70 mol percent and the sum of PEA and sodium hydroxide adds up to at least 100 mol percent.

TABLE I

Evaluation of the effect of variations in the mol % of PEA and NaOH on the optical purity and yield of (+)-2-(p-difluoromethoxyphenyl)-3-methylbutyric acid

| No | Toluene/water ratio | mol % PEA | mol % NaOH | % crude+ product | $[\alpha]_D^{RT}$ CHCl$_3$ in degrees | % (+)-acid++ present in crude product | % yield of+ (+)-acid |
|---|---|---|---|---|---|---|---|
| 1 | 100/0 | 45 | — | 67.3** | 36.9 | 92.0 | 61.9** |
| 2 | 55/45 | 40 | 50 | 71.6 | 39.1 | 97.3 | 69.7 |
| 3 | 50/50 | 45 | 55 | 88.2** | 33.0 | 87.5 | 77.2** |
| 4 | 55/45 | 50 | 40 | 76.1 | 31.3 | 87.8 | 66.8 |

TABLE I-continued

Evaluation of the effect of variations in the mol % of PEA and NaOH on the optical purity and yield of (+)-2-(p-difluoromethoxyphenyl)-3-methylbutyric acid

| No | Toluene/water ratio | mol % PEA | mol % NaOH | % crude+ product | $[\alpha]_D^{RT}$ CHCl$_3$ in degrees | % (+)-acid++ present in crude product | % yield of+ (+)-acid |
|----|---|---|---|---|---|---|---|
| 5  | 55/45 | 50 | 45 | 83.6    | 38.1 | 96.0  | 80.3   |
| 6  | 55/45 | 50 | 50 | 87.3*   | 36.8 | 95.6* | 83.5*  |
| 7  | 50/50 | 50 | 50 | 94.7**  | 32.5 | 87.0* | 82.4** |
| 8  | 55/45 | 50 | 60 | 85.4*   | 36.1 | 97.7  | 83.4** |
| 9  | 55/45 | 60 | 50 | 94.8*   | 37.0 | 95.8* | 90.8*  |
| 10 | 55/45 | 60 | 50 | 98.2*   | 37.4 | 95.9* | 94.2*  |
| 11 | 55/45 | 60 | 55 | 96.3*   | 38.2 | 95.2* | 91.7*  |
| 12 | 55/45 | 60 | 55 | 92.7    | 36.0 | 93.5  | 86.7   |
| 13 | 55/45 | 65 | 55 | 98.0    | 35.8 | 93.0  | 91.7   |
| 14 | 55/45 | 70 | 55 | 95.1    | 33.8 | 90.8  | 86.4   |
| 15 | 50/50 | 70 | 30 | 131.6** | 11.7 | 63.4  | 83.4** |

+ = purity of racemic acid included in calculations, excepting data marked with:**
++ = calculated from optical rotation data
* = chemical purity of (+) acid was included in these calculations

EXAMPLE 4

Comparison of the use of toluene and xylene in the resolution of the racemic mixture and the results obtained thereby By the methods of Examples 1 and 2, excepting that 4.1 kg of racemic acid is used in each test, the use of toluene and xylene on the resolution of racemic acid is compared. The results obtained are shown below.

|  | Toluene | Xylene |
|---|---|---|
| % yield of as is (+)-acid | 83.9 | 85.5 |
| $[\alpha]_D^{RT}$ methanol, in degrees | 36.8 | 34.6 |
| % (+)-acid | 91.9 | 89.4 |
| chemical purity of (+)-acid (%) | 97.7 | 98.6 |
| % real yield | 77.1 | 76.4 |

Comparable results are obtained using benzene as a solvent.

What is claimed is:

1. A method for the isolation of dextrorotatory 2-(p-difluoromethoxyphenyl)-3-methylbutyric acid comprising: admixing one molar equivalent of racemic 2-(p-difluoromethoxyphenyl)-3-methylbutyric acid in the presence of a mixture of water and a water immiscible solvent having a range of ratios of from 40/60 to 60/40 weight, with an optically active amine used in amounts sufficient to form a salt with the dextrorotatory component of said racemic acid, and an inorganic water soluble base used in amounts sufficient to total the sum of said base and of the above amine to at least 100 mol percent; heating the thus obtained mixture at a temperature range of from 40° C. to that of the boiling point of said mixture for a period of time sufficient to form the optically active amine salt of said dextrorotatory acid, isolating said salt from the rest of the reaction mixture and decomposing same with a mineral acid used in amounts sufficient to regenerate said dextrorotatory acid therefrom.

2. A method according to claim 1, wherein said water immiscible solvent is benzene, toluene or xylene; said optically active amine is (−)-α-phenethylamine, (+) and (−)-2-amino-1-butanol, dehydroabiethylamine, (+) and (−)-α-4-bromophenylethylamine, (−)-α-(1-naphthyl)ethylamine, 1-Ephedrine, 1S-2S-(+)-2-amino-1-phenyl-1, 3-propanediol, (+) and (−)-2-(4-chlorobenzylamino)-1-butanol, (+) and (−)-2-(4-thiobenzylamino)-1-butanol, (+) and (−)-2-(3-nitrobenzylamino)-1-butanol, or (+) and (−)-2-(2,5-dimethylbenzylamino)-1-butanol used in amounts of from 40 to 100 mol percent; said inorganic base is alkali metal hydroxides, carbonates, bicarbonates or ammonium hydroxide used in amounts of from 30 to 60 mol percent, and said acid is sulfuric acid or hydrochloric acid.

3. A method according to claim 2, wherein said water immiscible solvent is benzene, toluene or xylene; said optically active amine is (−)-α-phenethylamine used in amounts of from 40 to 100 mol percent; said inorganic base is alkali metal hydroxides, carbonates, bicarbonates or ammonium hydroxide, used in amounts of from 30 to 60 mol percent, and said acid is sulfuric acid or hydrochloric acid.

4. A method according to claim 3, wherein said solvent is toluene and the toluene:water ratio is from 50/50 to 55/45 by weight; (−)-α-phenethylamine is used in amounts of from 50 to 70 mol percent; said base is sodium hydroxide used in amounts of from 30 to 50 mol percent; the temperature of the reaction is of from 70° to 100° C., and said acid is sulfuric acid or hydrochloric acid.

5. A method according to claim 4, wherein the toluene:water ratio is 55/45 by weight, the amount of (−)-α-phenethylamine is 60 to 70 mol percent and the amount of sodium hydroxide is 30 to 50 mol percent, and the reaction temperature is 70° to 100° C.

* * * * *